(12) United States Patent
Felder et al.

(10) Patent No.: US 7,473,552 B2
(45) Date of Patent: Jan. 6, 2009

(54) PRODUCTION OF HYDROGEN GAS AND ISOLATION OF HYDROGEN PRODUCING MICROORGANISMS USING REPLENISHING COATED SUBSTRATES

(75) Inventors: Justin Felder, Hermitage, PA (US); Mitchell S. Felder, Hermitage, PA (US); Harry R. Diz, Erie, PA (US)

(73) Assignee: Nanologix, Inc., Hubbard, OH (US)

( * ) Notice: Subject to any disclaimer, the term of this patent is extended or adjusted under 35 U.S.C. 154(b) by 386 days.

(21) Appl. No.: 11/449,895

(22) Filed: Jun. 9, 2006

(65) Prior Publication Data

US 2006/0281158 A1    Dec. 14, 2006

Related U.S. Application Data

(60) Provisional application No. 60/692,598, filed on Jun. 21, 2005, provisional application No. 60/689,494, filed on Jun. 10, 2005.

(51) Int. Cl.
*C12P 3/00* (2006.01)
*C12M 1/00* (2006.01)
*C12M 1/16* (2006.01)

(52) U.S. Cl. .................... 435/303.2; 435/168

(58) Field of Classification Search ............... None
See application file for complete search history.

(56) References Cited

U.S. PATENT DOCUMENTS

| | | | |
|---|---|---|---|
| 4,198,211 A | 4/1980 | Shattock et al. |
| 4,274,838 A | 6/1981 | Dale et al. |
| 4,480,035 A | 10/1984 | Roychowdhury |
| 4,636,467 A | 1/1987 | Chynoweth |
| 4,670,397 A | 6/1987 | Wegner et al. |
| 4,761,376 A | 8/1988 | Kulpa et al. |
| 5,350,692 A | 9/1994 | Taguchi et al. |
| 5,387,271 A | 2/1995 | Crawford et al. |
| 5,464,539 A | 11/1995 | Ueno et al. |
| 5,554,520 A | 9/1996 | Fowler et al. |
| 5,705,374 A | 1/1998 | Sanford et al. |
| 5,707,825 A | 1/1998 | Oda |
| 5,746,919 A | 5/1998 | Dague et al. |
| 5,821,111 A | 10/1998 | Grady et al. |
| 6,008,028 A | 12/1999 | Bender et al. |
| 6,102,690 A | 8/2000 | Ingram et al. |
| 6,180,396 B1 | 1/2001 | Ono et al. |
| 6,270,731 B1 | 8/2001 | Kato et al. |
| 6,333,181 B1 | 12/2001 | Ingram et al. |
| 6,334,954 B1 | 1/2002 | Crawford et al. |
| 6,500,340 B1 | 12/2002 | Burke |
| 6,569,332 B2 | 5/2003 | Ainsworth et al. |
| 6,673,243 B2 | 1/2004 | Srinivasan et al. |
| 6,824,682 B2 | 11/2004 | Branson |
| 6,887,692 B2 | 5/2005 | Paterek |
| 6,936,170 B2 | 8/2005 | Shieh et al. |
| 6,942,798 B2 | 9/2005 | Miller, III |
| 6,942,998 B1 | 9/2005 | Ooteghem |
| 6,984,305 B2 | 1/2006 | McAlister |
| 2002/0148778 A1 | 10/2002 | Raven |
| 2003/0111410 A1 | 6/2003 | Branson |
| 2003/0205458 A1 | 11/2003 | Roychowdhury |
| 2004/0154982 A1 | 8/2004 | Irani |
| 2004/0224396 A1 | 11/2004 | Maston |
| 2004/0251197 A1 | 12/2004 | Chandler |
| 2005/0009159 A1 | 1/2005 | Paterek |
| 2005/0011829 A1 | 1/2005 | Dong et al. |
| 2005/0064567 A1 | 3/2005 | Lay et al. |
| 2005/0077029 A1 | 4/2005 | Cervantes et al. |
| 2005/0102673 A1 | 5/2005 | DeWitt, Jr. et al. |
| 2005/0176131 A1 | 8/2005 | Flickinger et al. |
| 2006/0011491 A1 | 1/2006 | Logan et al. |
| 2006/0019134 A1 | 1/2006 | Yagi et al. |
| 2006/0060526 A1 | 3/2006 | Binning et al. |
| 2007/0048850 A1* | 3/2007 | Diz et al. ............ 435/168 |
| 2007/0048851 A1* | 3/2007 | Diz et al. ............ 435/168 |

* cited by examiner

*Primary Examiner*—Herbert J. Lilling
(74) *Attorney, Agent, or Firm*—Carol A. Marmo; Eckert Seamans Cherin & Mellot, LLC

(57) ABSTRACT

The present invention provides a system of baiting and growing microorganisms on a gelatinous matrix. A bioreactor is provided wherein the bioreactor provides an environment conducive to the breakdown of organic aqueous material and the production of hydrogen from microorganisms and restrictive to the production of methane from methanogens. The bioreactor includes substrates coated with a gelatinous matrix, wherein the gelatinous matrix coating is replenished by additional coating material pumped into interior channels of the substrates wherein the substrates are permeable by the coating.

20 Claims, 5 Drawing Sheets

PRODUCTION OF HYDROGEN GAS AND ISOLATION OF HYDROGEN PRODUCING MICROORGANISMS USING REPLENISHING COATED SUBSTRATES

CROSS REFERENCE TO RELATED APPLICATIONS

The present application claims priority to U.S. Provisional Ser. Nos. 60/689,494 filed Jun. 10, 2005, entitled Hydrogen Producing Bioreactor With A Coated Pumping Means and 60/692,598 filed Jun. 21, 2005, entitled Hydrogen Producing Bioreactor.

FIELD OF THE INVENTION

The present invention relates generally to the concentrated isolation and growth of hydrogen generating microorganism cultures. More particularly, this invention relates to a bioreactor for the continuous growth of hydrogen using substrates coated with a gelatinous matrix. The continuous production is provided by microorganisms, such as hydrogen producing microorganisms, forming biofilm on the coated substrates, wherein the bioreactor provides an environment conducive to hydrogen production and restrictive to methane production.

BACKGROUND OF THE INVENTION

The production of hydrogen is an increasingly common and important procedure in the world today. Production of hydrogen in the U.S. alone currently amounts to about 3 billion cubic feet per year, with output likely to increase. Uses for the produced hydrogen are varied, ranging from uses in welding, in production of hydrochloric acid, and for reduction of metallic ores. An increasingly important use of hydrogen, however, is the use of hydrogen in fuel cells or for combustion. This is directly related to the production of alternative fuels for machinery, such as motor vehicles. Successful use of hydrogen as an alternative fuel can provide substantial benefits to the world at large. This is possible not only because hydrogen is produced without dependence on the location of specific oils or other ground resources, but because burning hydrogen is atmospherically clean. Essentially, no carbon dioxide or greenhouse gasses are produced when burning hydrogen. Thus, production of hydrogen as a fuel source can have great impact on the world at large.

For instance, electrolysis, which generally involves the use of electricity to decompose water into hydrogen and oxygen, is a commonly used process. Significant energy, however, is required to produce the needed electricity to perform the process. Similarly, steam reforming is another expensive method requiring fossil fuels as an energy source. As could be readily understood, the environmental benefits of producing hydrogen are at least partially offset when using a process that uses pollution-causing fuels as an energy source for the production of hydrogen.

There is further need in environmental interests for new developments of biodegredation. Biodegredation refers to the degradation of sewages, effluents, toxic substances or other material organic material by microorganisms. The breakdown of toxic substances is also known as bioremeduiation. Biodegredation typically occurs in anarobic environments, and is generallys the process of converting organic materials back into $CO_2$ and/or $H_2O$ through microbial action. Biodegredation is useful in that it breaks down unwanted or uneeded organic substances into natureal substances. However, a typical biodegradation product results in the formation of methane. Methane has a hgreenhouse gas having a high level of global warming potential. Excessive release of methane into the atmosphere is highly undesireable.

Thus, producing hydrogen from biological systems, through biodegradation or bioremediation, wherein the energy for the process is substantially provided by naturally occurring bacteria, is an optimal solution. Fermentation of organic matter by hydrogen producing microorganisms, such as *Bacillus* or *Clostridium,* is one such method. Nonetheless, hydrogen production relating to the above methods has remained problematic, and the need remains for the ability to optimize yields of hydrogen while minimizing expenditures.

New methods of hydrogen generation are needed. One possible method is to convert waste organic matter into hydrogen gas. Microbiologists have for many years known of organisms which generate hydrogen as a metabolic by-product. Two reviews of this body of knowledge are Kosaric and Lyng (1988) and Nandi and Sengupta (1998). Among the various organisms mentioned, the heterotrophic facultative anaerobes are of interest in this study, particularly those in the group known as the enteric bacteria. Within this group are the mixed-acid fermenters, whose most well known member is *Escherichia coli.* While fermenting glucose, these bacteria split the glucose molecule forming two moles of pyruvate (Equation 1); an acetyl group is stripped from each pyruvate fragment leaving formic acid (Equation 2), which is then cleaved into equal amounts of carbon dioxide and hydrogen as shown in simplified form below (Equation 3).

$$\text{Glucose} \rightarrow 2\text{Pyruvate} \tag{1}$$

$$2\text{Pyruvate} + 2\text{Coenzyme A} \rightarrow 2\text{Acetyl-CoA} + 2\text{HCOOH} \tag{2}$$

$$2\text{HCOOH} \rightarrow 2H_2 + 2CO_2 \tag{3}$$

Thus, during this process, one mole of glucose produces two moles of hydrogen gas. Also produced during the process are acetic and lactic acids, and minor amounts of succinic acid and ethanol. Other enteric bacteria (the 2, 3 butanediol fermenters) use a different enzyme pathway which causes additional $CO_2$ generation resulting in a 6:1 ratio of carbon dioxide to hydrogen production (Madigan et al., 1997).

There are many sources of waste organic matter which could serve as a substrate for this microbial process, namely as a provider of pyruvate. One such attractive material would be organic-rich industrial wastewaters, particularly sugar-rich waters, such as fruit and vegetable processing wastes. In additional embodiments, wastewaters rich not only in sugars but also in protein and fats could be used, such as milk product wastes. The most complex potential source of energy for this process would be sewage-related wastes, such as municipal sewage sludge and animal manures.

The creation of a gas product that includes hydrogen can be achieved in a bioreactor, wherein hydrogen producing microorganisms and a food source are held in a reactor environment favorable to hydrogen production. Substantial, systematic and useful creation of hydrogen gas from microorganisms, however, is problematic. The primary obstacle to sustained production of useful quantities of hydrogen by microorganisms has been the eventual stoppage of hydrogen production, generally coinciding with the appearance of methane. This occurs when methanogenic bacteria invade the reactor environment converting hydrogen to methane, typically under the reaction $CO_2 + 4H_2 \rightarrow CH_4 + 2H_2O$. This process occurs naturally in anaerobic environments such as marshes, swamps, pond sediments, and human intestines.

It is of further importance to increase the number of hydrogen producing microorganisms in a system to the point that fixed colonies of biofilm are existent in the bioreactor. Increasing the number of hydrogen producing microorganisms and biofilm and thereby increasing the overall percentage of hydrogen producing microorganisms is beneficial, particularly in large scale reactors. Therefore, it is important to create a bioreactor environment that is conducive to hydrogen producing microorganism growth and maintenance in addition to hydrogen production.

Thus, there continually remains a need to produce substantial and useful levels of hydrogen in an a system that provides an environment conducive to metabolism of organic feed material by hydrogen producing microorganisms.

SUMMARY OF THE INVENTION

The present invention provides a system for aiding the growth of biofilm in a bioreactor, wherein the biofilm is a hydrogen producing microorganisms containing biofilm, wherein replenishably coated substrates are provided within the bioreactor for the growth of biofilm thereon.

It is further object of the invention to provide a system for producing hydrogen and isolating microorganisms having an anaerobic bioreactor for holding organic feed material and adapted to produce hydrogen from hydrogen producing microorganisms metabolizing the organic feed material, and one or a multiplicity of substrates contained within the bioreactor, the one or a multiplicity of substrates having a coating disposed thereon for hosting the growth of biofilm, wherein the coating is a replenishable coating from a coating source outside the bioreactor.

It is a further object of the invention to provide a system a system for producing hydrogen and isolating microorganisms having an anaerobic bioreactor for holding organic feed material and adapted to produce hydrogen from hydrogen producing microorganisms metabolizing the organic feed material, one or a multiplicity of substrates contained within the bioreactor, the one or a multiplicity of substrates having a permeable or semi-permeable surface portion, a channel portion interior the surface portion, wherein the channel accessible from outside the bioreactor, a coating container for holding a coating, and a coating passage for conveying the coating from the coating container to the channel portions of the one or a multiplicity of substrates.

It is a further object of the invention to provide a coating pump is operably related to the coating passage.

It is a further object of the invention to provide a coating that a gelatinous matrix coating, the gelatinous matrix coating formed from agar and at least one carbon compound.

It is a further object of the invention to provide a carbon compound selected form the group consisting of glucose, fructose, glycerol, mannitol, asparagines, casein, adonitol, l-arabinose, cellobiose, dextrose, dulcitol, d-galactose, inositol, lactose, levulose, maltose, d-mannose, melibiose, raffinose, rhamnose, sucrose, salicin, d-sorbitol, d-xylose or combinations thereof.

It is a further object of the invention to provide a system wherein additional coating is introduced into a channel portion of one or a multiplicity of substrates, the additional coating permeating though the surface portion of the one or a multiplicity of substrates to replenish the replenishable coating.

These and other objects of the present invention will become more readily apparent from the following detailed description and appended claims.

DETAILED DESCRIPTION OF PREFERRED EMBODIMENTS

As used herein, the term "microorganisms" include bacteria and substantially microscopic cellular organisms.

As used herein, the term "hydrogen producing microorganisms" includes microorganisms that metabolize an organic substrate in one or a series of reactions that ultimately form hydrogen as one of the end products.

As used herein, the term "methanogens" refers to microorganisms that metabolize hydrogen in one or a series of reactions that produce methane as one of the end products.

As used herein, the term "replenishable coating" refers to coating that can be replaced or supplemented by the introduction of additional coating.

Figure 1:
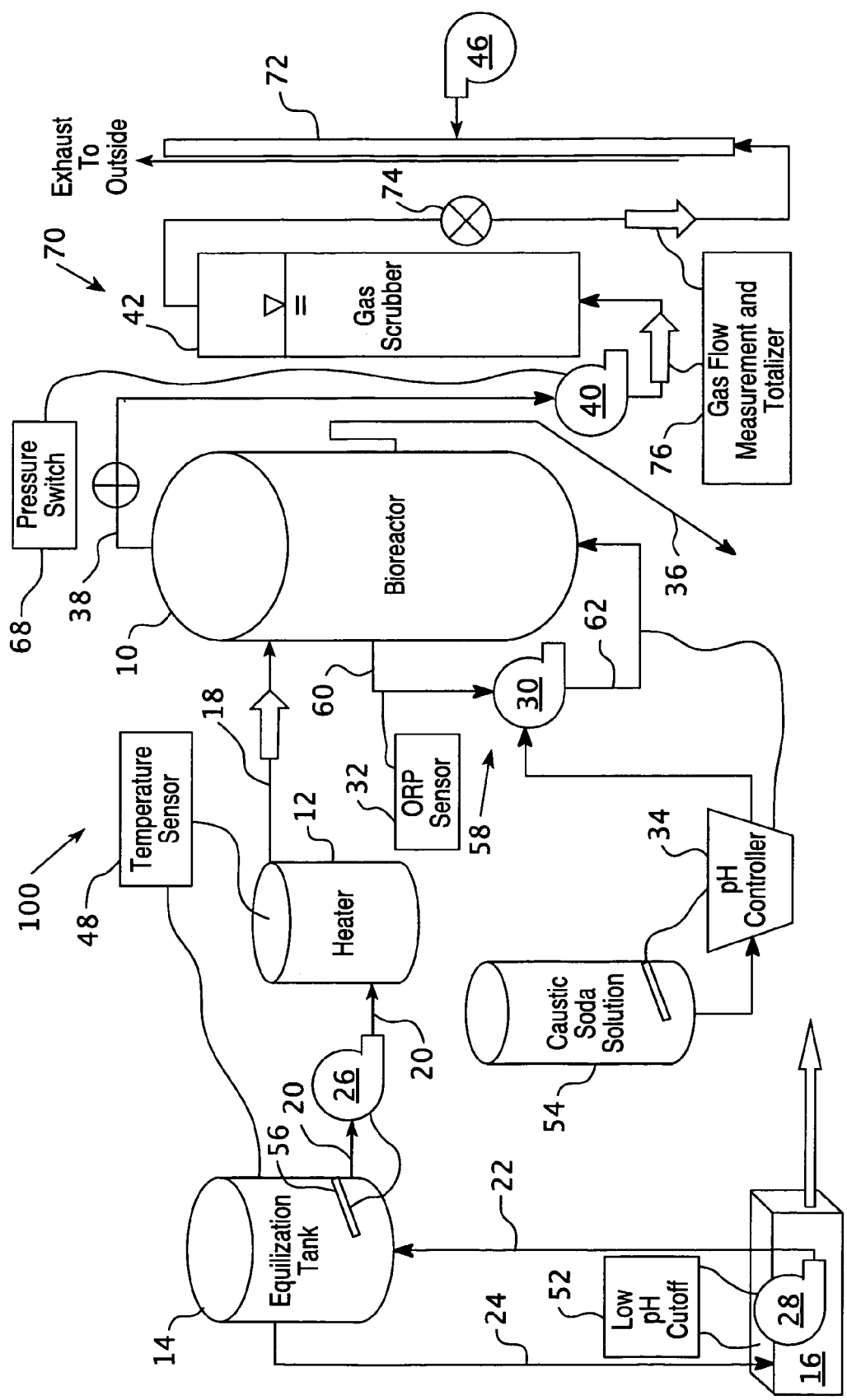
FIG. 1 is a plan view of the hydrogen production system.

A hydrogen producing system 100 for sustained production of hydrogen in accordance with the present invention is shown in FIG. 1, including bioreactor 10, heater 12, equalization tank 14 and reservoir 16. The apparatus enables the production of sustained hydrogen containing gas in bioreactor 10, wherein the produced gas substantially produces a 1:1 ratio of hydrogen to carbon dioxide gas and does not substantially include any methane. The hydrogen containing gas is produced by the metabolism of an organic feed material by hydrogen producing microorganisms. In preferred embodiments, organic feed material is a sugar containing aqueous solution. In further preferred embodiments, the organic feed material is industrial wastewater or effluent product that is produced during routine formation of fruit and/or vegetable juices, such as grape juice. In additional embodiments, wastewaters rich not only in sugars but also in protein and fats could be used, such as milk product wastes. The most complex potential source of energy for this process would be sewage-related wastes, such as municipal sewage sludge and animal manures. However, any organic feed material containing organic material is usable in hydrogen producing apparatus 100. Hydrogen producing microorganisms metabolize the sugars in the organic feed material under the reactions:

$$\text{Glucose} \rightarrow 2\text{Pyruvate} \tag{1}$$

$$2\text{Pyruvate} + 2\text{Coenzyme A} \rightarrow 2\text{Acetyl-CoA} + 2\text{HCOOH} \tag{2}$$

$$2\text{HCOOH} \rightarrow 2\text{H}_2 + 2\text{CO}_2 \tag{3}$$

During this process, one mole of glucose produces two moles of hydrogen gas and carbon dioxide. In alternate embodiments, other organic feed materials include agricultural residues and other organic wastes such as sewage and manures. Typical hydrogen producing microorganisms are adept at metabolizing the high sugar organic waste into bacterial waste products. The organic feed material may be further treated by aerating, diluting the organic feed material with water or other dilutants, adding compounds that can control the pH of the organic feed material or other treatment step. For example, the organic feed material may be supplemented with phosphorus ($NaH_2PO_4$) or yeast extract.

Organic feed material provides a plentiful feeding ground for hydrogen producing microorganisms and is naturally infested with these microorganisms. While hydrogen producing microorganisms typically occur naturally in an organic feed material, the organic feed material is preferably further inoculated with hydrogen producing microorganisms in an inoculation step. The inoculation may be an initial, one-time addition to bioreactor 10 at the beginning of the hydrogen production process. Further inoculations, however, may be added as desired. The added hydrogen producing microorganisms may include the same types of microorganisms that occur naturally in the organic feed material. In preferred embodiments, the hydrogen producing microorganisms, whether occurring naturally or added in an inoculation step, are preferably microorganisms that thrive in pH levels of about 3.5 to 6.0 and can survive at elevated temperatures. These hydrogen producing microorganisms include, but are not limited to, *Clostridium sporogenes, Bacillus lichenformis* and *Kleibsiella oxytoca*. Hydrogen producing microorganisms can be obtained from a microorganisms culture lab or like source. Other hydrogen producing microorganisms or microorganisms known in the art, however, can be used within the spirit of the invention. The inoculation step can occur in bioreactor 10 or elsewhere in the apparatus, for example, circulation system 58.

Reservoir 16 is a container known in the art that can contain an organic feed material. The size, shape, and material of reservoir 16 can vary widely within the spirit of the invention. In one embodiment, reservoir 16 is one or a multiplicity of storage tanks that are adaptable to receive, hold and store the organic feed material when not in use, wherein the one or a multiplicity of storage tanks may be mobile. In preferred embodiments, reservoir 16 is a wastewater well that is adaptable to receive and contain wastewater and/or effluent from an industrial process. In further preferred embodiments, reservoir 16 is adaptable to receive and contain wastewater that is effluent from a juice manufacturing industrial process, such that the effluent held in the reservoir is a sugar rich juice sludge.

Organic feed material contained in reservoir 16 can be removed through passage 22 with pump 28. Pump 28 is in operable relation to reservoir 16 such that it aids removal movement of organic feed material 16 into passage 22 at a desired, adjustable flow rate, wherein pump 28 can be any pump known in the art suitable for pumping liquids. In a preferred embodiment, pump 28 is a submersible sump pump. Reservoir 16 may further include a low pH cutoff device 52, such that exiting movement into passage 22 of the organic feed material is ceased if the pH of the organic feed material is outside of a desired range. The pH cutoff device 52 is a device known in the art operably related to reservoir 16 and pump 28. If the monitor detects a pH of a organic feed material in reservoir 16 out of range, the device ceases operation of pump 28. The pH cut off in reservoir 16 is typically greater than the preferred pH of bioreactor 10. In preferred embodiments, the pH cutoff 52 is set between about 7 and 8 pH. In alternate embodiments, particularly when reservoir 16 is not adapted to receive effluent from an industrial process, the pH cutoff device is not used.

Passage 22 provides further entry access into equalization tank 14 or heater 12. Equalization tank is an optional intermediary container for holding organic feed material between reservoir 16 and heater 12. Equalization tank 14 provides an intermediary container that can help control the flow rates of organic feed material into heater 12 by providing a slower flow rate into passage 20 than the flow rate of organic feed material into the equalization tank through passage 22. The equalization tank can be formed of any material suitable for holding and treating the organic feed material. In the present invention, equalization tank 14 is constructed of high density polyethylene materials. Other materials include, but are not limited to, metals or plastics. Additionally, the size and shape of equalization tank 14 can vary widely within the spirit of the invention depending on output desired and location limitations. In preferred embodiments, equalization tank 14 further includes a low level cut-off point device 56. The low-level cut-off point device ceases operation of pump 26 if organic feed material contained in equalization tank 14 falls below a predetermined level. This prevents air from entering passage 20. Organic feed material can be removed through passage 20 or through passage 24. Passage 20 provides removal access from equalization tank 14 and entry access into heater 12. Passage 24 provides removal access from equalization tank 14 of organic feed material back to reservoir 16. Passage 24 provides a removal system for excess organic feed material that exceeds the cut-off point of equalization tank 14. Both passage 20 and passage 24 may further be operably related to pumps to facilitate movement of the organic feed material. In alternate embodiments, equalization tank 14 is not used and organic feed material moves directly from reservoir 16 to heater 12. In these embodiments, passages connecting reservoir 16 and heater 12 are arranged accordingly.

The organic feed material is optionally heated prior to introduction into the bioreactor. The heating can occur anywhere upstream. In one embodiment, the heating is achieved in heater 12, wherein the organic feed material is heated within the heater. Alternatively, organic feed material can be heated at additional or alternate locations in the hydrogen production system. Passage 20 provides entry access to heater 12, wherein heater 12 is any apparatus known in the art that can contain and heat contents held within it. Passage 20 is preferably operably related to pump 26. Pump 26 aids the conveyance of organic feed material from equalization tank 14 or reservoir 16 into heater 12 through passage 20, wherein pump 26 is any pump known in the art suitable for this purpose. In preferred embodiments, pump 26 is an air driven pump for ideal safety reasons. However, motorized pumps are also found to be safe and are likewise usable.

To allow hydrogen producing microorganisms within the bioreactor 10 to metabolize the organic feed material and produce hydrogen without subsequent conversion of the hydrogen to methane by methanogens, methanogens contained within the organic feed material are substantially killed or deactivated. In preferred embodiments, the methanogens are substantially killed or deactivated prior to entry into the bioreactor. In further preferred embodiments, methanogens contained within the organic feed material are substantially killed or deactivated by being heated under elevated temperatures in heater 12. Methanogens are substantially killed or deactivated by elevated temperatures. Methanogens are generally deactivated when heated to temperatures of about 60-75° C. for a period of at least 15 minutes. Additionally, methanogens are generally damaged or killed when heated to temperatures above about 90° C. for a period of at least 15 minutes. In contrast, many hydrogen producing microorganisms are resistant to temperatures up to about 110° C. for over three hours. Heater 12 enables heating of the organic feed material to temperature of about 60 to 100° C. in order to substantially deactivate or kill the methanogens while leaving any hydrogen producing microorganisms substantially functional. This effectively pasteurizes or sterilizes the contents of the organic feed material from active methanogens while leaving the hydrogen producing microorganisms intact, thus allowing the produced biogas to include hydrogen without subsequent conversion to methane. Heater 12 can be any receptacle known in the art for holding, receiving and conveying the organic feed material. Similar to the equalization tank 14, heater 12 is preferably formed substantially from metals, acrylics, other plastics or combinations thereof, yet the material can vary widely within the spirit of the invention to include other suitable materials. Similarly, the size and the shape of heater 12 can vary widely within the spirit of the invention depending on output required and location limitations. In preferred embodiments, retention time in heater 12 is at least one hour.

At least one temperature sensor 48 monitors a temperature indicative of the organic feed material temperature, preferably the temperature levels of equalization tank 14 and/or heater 12. In preferred embodiments, an electronic controller is provided having at least one microprocessor adapted to process signals from one or a plurality of devices providing organic feed material parameter information, wherein the electronic controller is operably related to the at least one actuatable terminal and is arranged to control the operation of and to controllably heat the heating tank and/or any contents therein. The electronic controller is located or coupled to heater 12 or equalization tank 14, or can alternatively be at a third or remote location. In alternate embodiments, the controller for controlling the temperature of heater 12 is not operably related to temperature sensor 48.

Passage 18 connects heater 12 with bioreactor 10. Organic feed material is conveyed into the bioreactor through transport passage 18 at a desired flow rate. System 100 is a continuous flow system with organic feed material in constant motion between containers such as reservoir 16, heater 12, bioreactor 10, equalization tank 14 if applicable, and so forth. Flow rates between the container can vary depending on retention time desired in any particular container. For example, in preferred embodiments, retention time in bioreactor 10 is between about 6 and 12 hours. To meet this retention time, the flow rate of passage 18 and effluent passage 38 are adjustable as known in the art so that organic feed material, on average, stays in bioreactor 10 for this period of time.

The organic feed material is conveyed through passage 18 having a first and second end, wherein passage 18 provides entry access to the bioreactor at a first end of passage 18 and providing removal access to the heater at a second end of passage 18. Any type of passage known in the art can be used, such as a pipe or flexible tube. The transport passage may abut or extend within the bioreactor and/or the heater. Passage 18 can generally provide access into bioreactor 10 at any location along the bioreactor. However, in preferred embodiments, passage 18 provides access at an upper portion of bioreactor 10.

Bioreactor 10 provides an anaerobic environment conducive for hydrogen producing microorganisms to grow, metabolize organic feed material, and produce hydrogen. While the bioreactor is beneficial to the growth of hydrogen producing microorganisms and the corresponding metabolism of organic feed material by the hydrogen producing microorganisms, it is preferably restrictive to the proliferation of methanogens, wherein methanogens are microorganisms that metabolize carbon dioxide and hydrogen to produce methane and water. Methanogens are obviously unwanted as they metabolize hydrogen. If methanogens were to exist in substantial quantities in bioreactor 10, hydrogen produced by the hydrogen producing microorganisms will subsequently be converted to methane, reducing the percentage of hydrogen in the produced gas.

Bioreactor 10 can be any receptacle known in the art for carrying an organic feed material. Bioreactor 10 is substantially airtight, providing an anaerobic environment. Bioreactor 10 itself may contain several openings. However, these openings are covered with substantially airtight coverings or connections, such as passage 18, thereby keeping the environment in bioreactor 10 substantially anaerobic. Generally, the receptacle will be a limiting factor in the amount of material that can be produced. The larger the receptacle, the more hydrogen producing microorganisms containing organic feed material, and, by extension, hydrogen, can be produced. Therefore, the size and shape of the bioreactor can vary widely within the sprit of the invention depending on output desired and location limitations.

Figure 2:
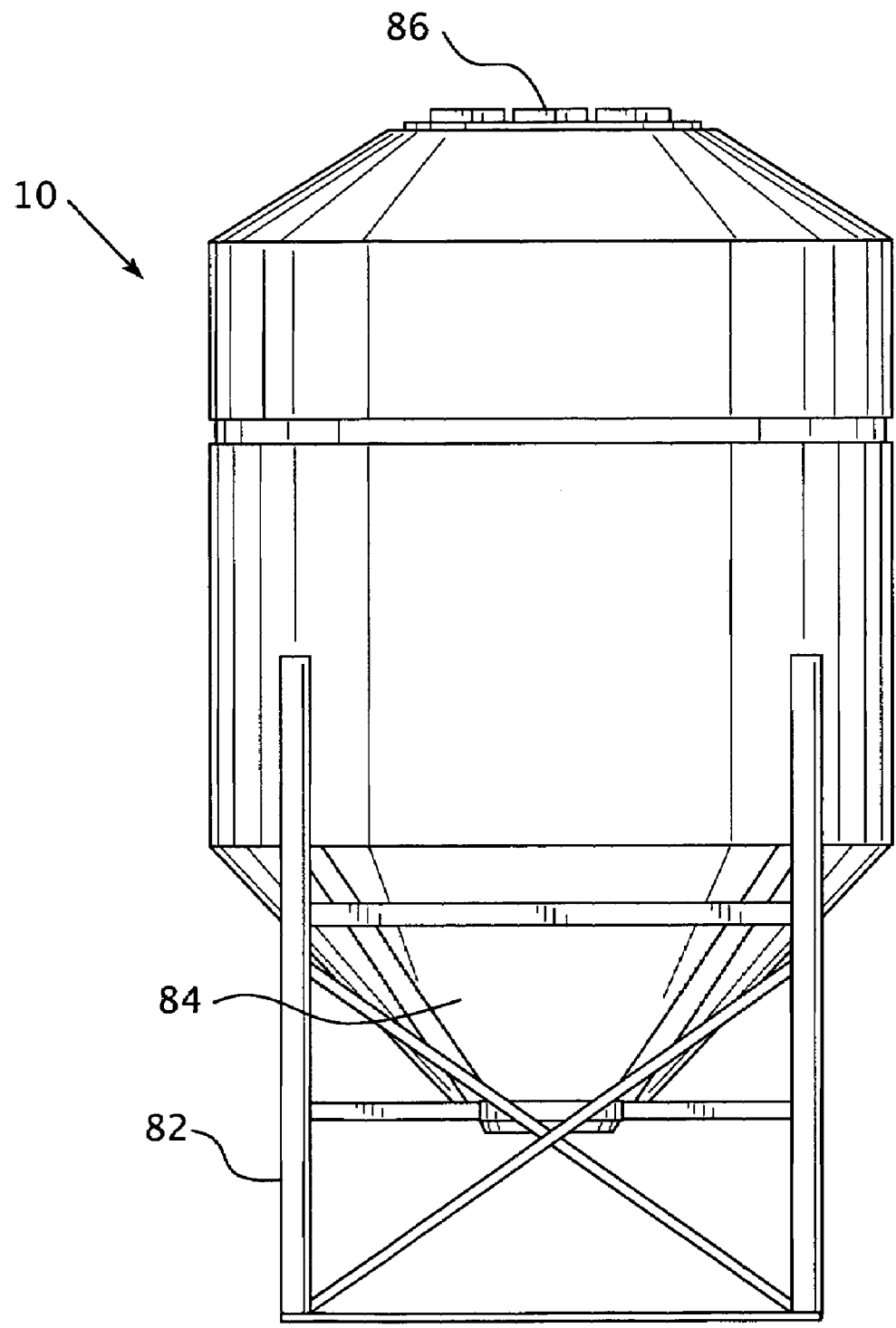
FIG. 2 is a side view of one embodiment of the bioreactor.

A preferred embodiment of a bioreactor is shown in FIG. 2. Bioreactor 10 can be formed of any material suitable for holding an organic feed material and that can further create an airtight, anaerobic environment. In the present invention, bioreactor 10 is constructed of high density polyethylene materials. Other materials, including but not limited to metals or plastics, can similarly be used. A generally silo-shaped bioreactor 10 has about a 300 gallon capacity with a generally conical bottom 84. Stand 82 is adapted to hold cone bottom 84 and thereby hold bioreactor 10 in an upright position. The bioreactor 10 preferably includes one or a multiplicity of openings that provide a passage for supplying or removing contents from within the bioreactor. The openings may further contain coverings known in the art that cover and uncover the openings as desired. For example, bioreactor 10 preferably includes a central opening covered by lid 86. In alternate embodiments of the invention, the capacity of bioreactor 10 can be readily scaled upward or downward depending on needs or space limitations.

Figure 3:
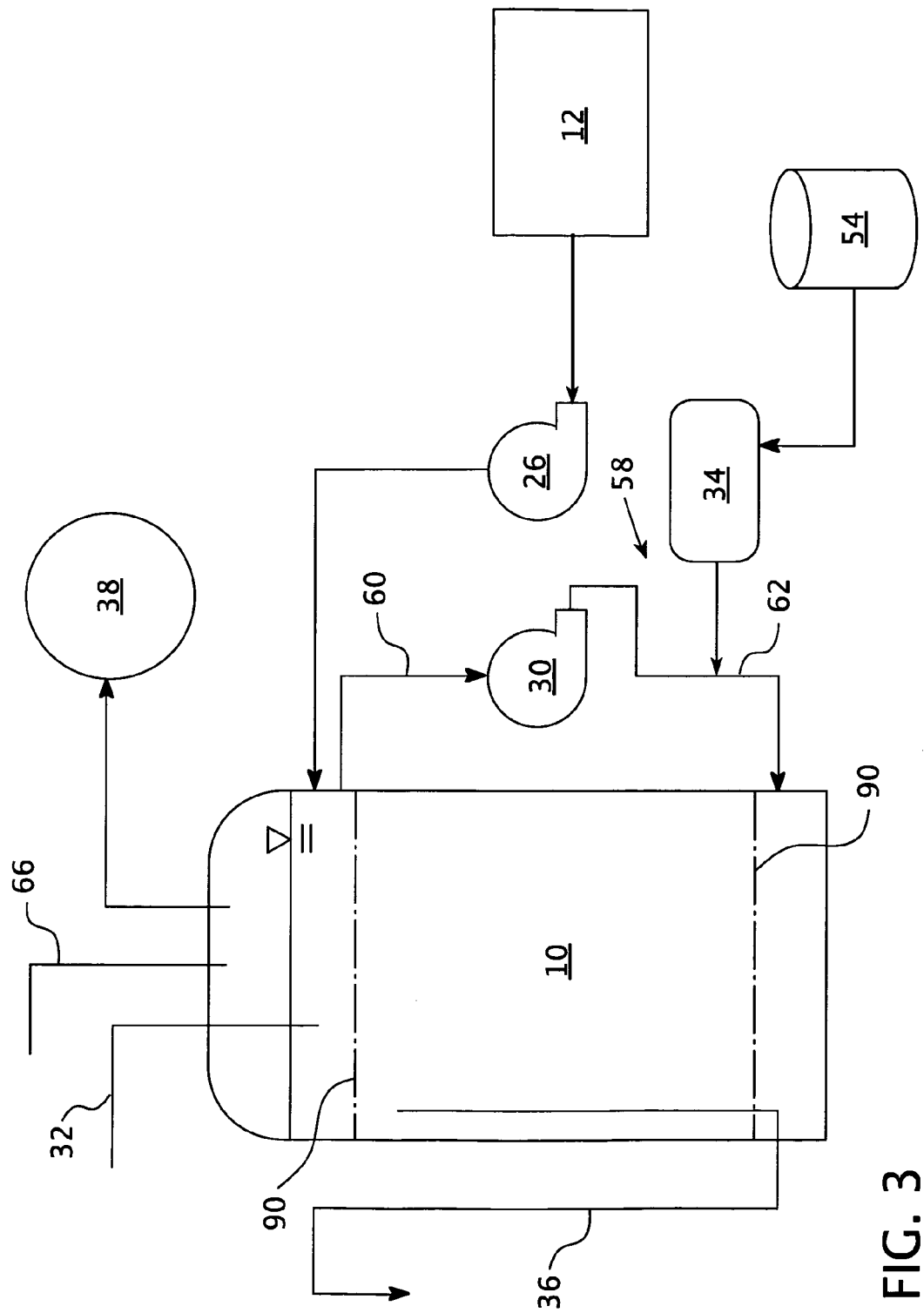
FIG. 3 is a plan view the bioreactor.

To maintain the organic feed material volume level at a generally constant level, the bioreactor preferably provides a system to remove excess organic feed material, as shown in FIGS. 1 and 3. In the present embodiment, the bioreactor includes effluent passage 36 having an open first and second end that provides a passage from inside bioreactor 10 to outside the bioreactor. The first end of effluent passage 36 may abut bioreactor 10 or extend into the interior of bioreactor 10. If effluent passage 36 extends into the interior of passage 10, the effluent tube preferably extends upwards to generally upper portion of bioreactor 10. When bioreactor 10 is filled with organic feed material, the open first end of the effluent passage allows an excess organic feed material to be received by effluent passage 36. Effluent passage 36 preferably extends from bioreactor 10 into a suitable location for effluent, such as a sewer or effluent container, wherein the excess organic feed material will be deposited through the open second end.

Figure 4:
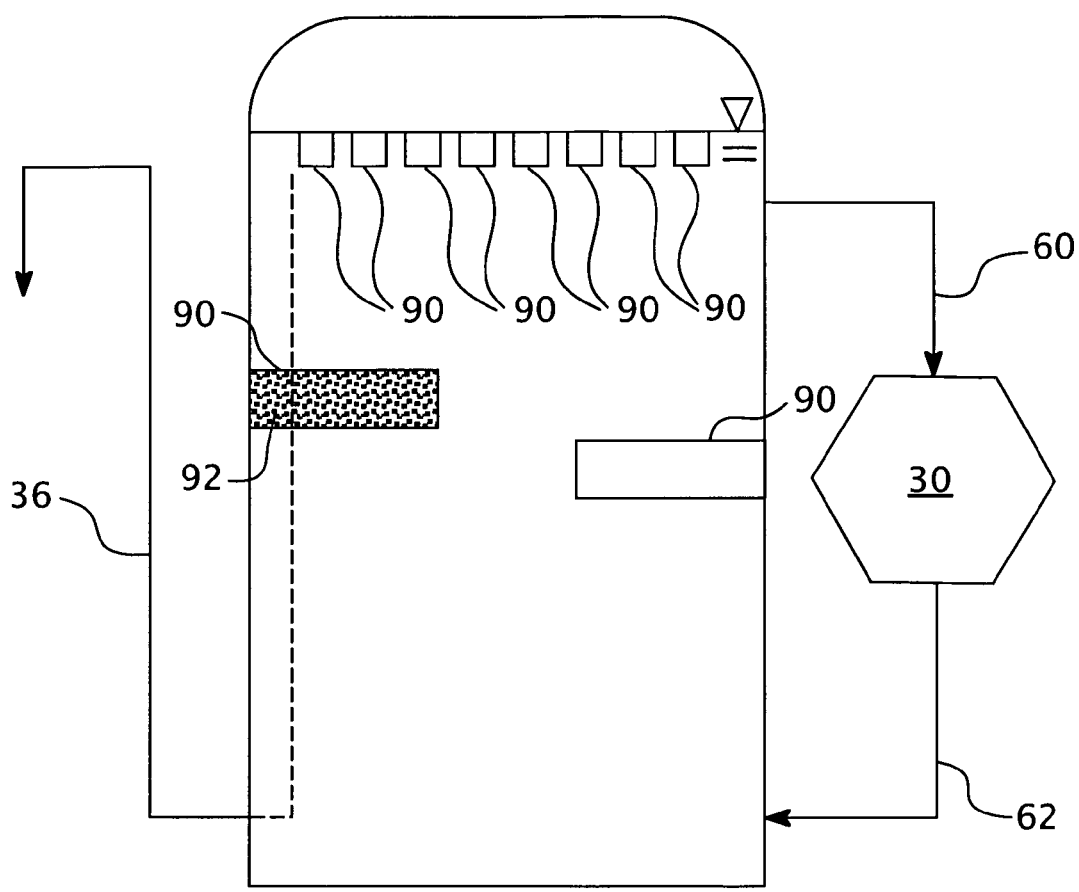
FIG. 4 is a plan view of coated substrates.

Bioreactor 10 preferably contains one or a multiplicity of substrates 90, as shown in FIG. 4, for providing surface area for attachment and growth of bacterial biofilms. Sizes and shapes of the one or a multiplicity of substrates 90 can vary widely, including but not limited to flat surfaces, pipes, rods, beads, slats, tubes, slides, screens, honeycombs, spheres, object with latticework, or other objects with holes bored through the surface. Numerous substrates can be used, for example, hundreds, as needed. The more successful the biofilm growth on the substrates, the more fixed state hydrogen production will be achieved. The fixed nature of the hydrogen producing microorganisms provide the sustain production of hydrogen in the bioreactor.

Substrates 90 preferably are substantially free of interior spaces that potentially fill with gas. In the present embodiment, the bioreactor comprises about 100-300 pieces of 1"

plastic media to provide surface area for attachment of the bacterial biofilm. In one embodiment, substrates 90 are Flexiring™ Random Packing (Koch-Glitsch.) Some substrates 90 may be retained below the liquid surface by a retaining device, for example, a perforated acrylic plate. In this embodiment, substrates 90 have buoyancy, and float on the organic feed material. When a circulation system is operably, the buoyant substrates stay at the same general horizontal level while the organic feed material circulates, whereby providing greater access to the organic feed material by hydrogen producing microorganism- and microorganism-containing biofilm growing on the substrates.

In preferred embodiments, a circulation system 58 is provided in operable relation to bioreactor 10. Circulation system 58 enables circulation of organic feed material contained within bioreactor 10 by removing organic feed material at one location in bioreactor 10 and reintroduces the removed organic feed material at a separate location in bioreactor 10, thereby creating a directional flow in the bioreactor. The directional flow aids the microorganisms within the organic feed material in finding food sources and substrates on which to grown biofilms. As could be readily understood, removing organic feed material from a lower region of bioreactor 10 and reintroducing it at an upper region of bioreactor 10 would create a downward flow in bioreactor 10. Removing organic feed material from an upper region of bioreactor 10 and reintroducing it at a lower region would create an up-flow in bioreactor 10.

In preferred embodiments, as shown in FIG. 1, circulation system 58 is arranged to produce an up-flow of any organic feed material contained in bioreactor 10. Passage 60 provides removal access at a higher point than entry access provided is provided by passage 62. Pump 30 facilitates movement from bioreactor 10 into passage 60, from passage 60 into passage 62, and from passage 62 back into bioreactor 10, creating up-flow movement in bioreactor 10. Pump 30 can be any pump known in the art for pumping organic feed material. In preferred embodiments, pump 30 is an air driven centrifugal pump. Other arrangements can be used, however, while maintaining the spirit of the invention. For example, a pump could be operably related to a single passage that extends from one located of the bioreactor to another.

Bioreactor 10 may optionally be operably related to one or a multiplicity of treatment apparatuses for treating organic feed material contained within bioreactor 10 for the purpose of making the organic feed material more conducive to proliferation of hydrogen producing microorganisms. The one or a multiplicity of treatment apparatuses perform operations that include, but are to limited to, aerating the organic feed material, diluting the organic feed material with water or other dilutant, controlling the pH of the organic feed material, and adding additional chemical compounds to the organic feed material. The apparatus coupled to the bioreactor can be any apparatuses known in the art for incorporating these treatments. For example, in one embodiment, a dilution apparatus is a tank having a passage providing controllable entry access of a dilutant, such as water, into bioreactor 10. An aerating apparatus is all apparatus known in the art that provides a how of gas into bioreactor 10, wherein the gas is typically air. A pH control apparatus is an apparatus known in the art for controlling a pH of a organic feed material. Additionally chemical compounds added by treatment apparatuses include anti-fungal agents, phosphorous supplements, yeast extract or hydrogen producing microorganisms inoculation. In other embodiments, the one or a multiplicity of treatment apparatuses may be operably related to other parts of the bioreactor system. For example, in one example, the treatment apparatuses are operably related to equalization tank 14 or circulation system 58. In still other embodiments, multiple treatment apparatus of the same type may be located at various points in the bioreactor system to provide treatments at desired locations.

Certain hydrogen producing microorganisms proliferate in pH conditions that are not favorable to methanogens, for example, *Kleibsiella oxytoca*. Keeping organic feed material contained within bioreactor 10 within this favorable pH range is conducive to hydrogen production. Controlling pH in the bioreactor may be performed alternatively or additionally lo heating waste material prior to introduction into the bioreactor. In preferred embodiments, pH controller 34 monitors the pH level of contents contained within bioreactor 10. In preferred embodiments, the pH of the organic feed material in bioreactor 10 is maintained at about 3.5 to 6.0 pH, most preferably at about 4.5 to 5.5 pH, as shown in Table 2. In further preferred embodiments, pH controller 34 controllably monitors the pH level of the organic feed material and adjustably controls the pH of the organic feed material if the organic feed material falls out of or is in danger of falling out of the desired range. As shown in FIG. 1, pH controller 34 monitors the pH level of contents contained in passage 62, such as organic feed material, with a pH sensor (represented as the wavy line connecting pH controller 34 and passage 62.) As could readily be understood, pH controller 34 can be operably related to any additional or alternative location that potentially holds organic feed material, for example, passage 60, 62 or bioreactor 10 as shown in FIG. 3.

If the pH of the organic feed material falls out of a desired range, the pH is preferably adjusted back into the desired range. Control of a pH level provides an environment that enables at least some hydrogen producing microorganisms to function while similarly providing an environment unfavorable to methanogens. This enables the novel concept of allowing microorganisms reactions to create hydrogen without subsequently being overrun by methanogens that convert the hydrogen to methane. Control of pH of the organic feed material in the bioreactor can be achieved by any means known in the art. In one embodiment, a pH controller 34 monitors the pH and can add a pH control solution from container 54 in an automated manner if the pH of the organic feed material moves out of a desired range. In a preferred embodiment, the pH monitor controls the organic feed material's pH through automated addition of a sodium or potassium hydroxide solution. One such apparatus for achieving this is an Etatron DLX pH monitoring device. Preferred ranges of pH for the organic feed material is between about 3.5 and 6.0, with a more preferred range between about 4.0 and 5.5 pH.

The hydrogen producing reactions of hydrogen producing microorganisms metabolizing organic feed material in bioreactor 10 can further be monitored by oxidation-reduction potential (ORP) sensor 32. ORP sensor 32 monitors redox potential of aqueous organic feed material contained within bioreactor 10. Once ORP drops below about −200 mV, gas production commences. Subsequently while operating in a continuous flow mode, the ORP was typically in the range of −300 to −450 mV.

In one embodiment, the wastewater is a grape juice solution prepared using Welch's Concord Grape Juice™ diluted in chlorine-free tap water at approximately 32 mL of juice per Liter. Alternatively, the solution is aerated previously for 24 hours to substantially remove chlorine. Due to the acidity of the juice, the pH of the organic feed material is typically around 4.0. The constitutional make-up of the grape juice solution is shown in Table 1.

TABLE 1

Composition of concord grape juice. Source:
Welch's Company, personal comm., 2005.

| Constituent | Concentration (unit indicated) | |
|---|---|---|
| | Mean | Range |
| Carbohydrates[1] | | 15-18% |
| glucose | 6.2% | 5-8% |
| fructose | 5.5% | 5-8% |
| sucrose | 1.8% | 0.2-2.3% |
| maltose | 1.9% | 0-2.2% |
| sorbitol | 0.1% | 0-0.2% |
| Organic Acids[1] | | 0.5-1.7% |
| Tartaric acid | 0.84% | 0.4-1.35% |
| Malic acid | 0.86% | 0.17-1.54% |
| Citric acid | 0.044% | 0.03-0.12% |
| Minerals[1] | | |
| Calcium | | 17-34 mg/L |
| Iron | | 0.4-0.8 mg/L |
| Magnesium | | 6.3-11.2 mg/L |
| Phosphorous | | 21-28 mg/L |
| Potassium | | 175-260 mg/L |
| Sodium | | 1-5 mg/L |
| Copper | | 0.10-0.15 mg/L |
| Manganese | | 0.04-0.12 mg/L |
| Vitamins[1] | | |
| Vitamin C | | 4 mg/L |
| Thiamine | | 0.06 mg/L |
| Riboflavin | | 0.04 mg/L |
| Niacin | | 0.2 mg/L |
| Vitamin A | | 80 I.U. |
| pH | | 3.0-3.5 |
| Total solids | | 18.5% |

[1]additional trace constituents in these categories may be present.

Bioreactor 10 further preferably includes an overflow cut-off switch 66, as shown in FIG. 3, to turn off feed pump 26 if the organic feed material exceeds or falls below a certain level in the bioreactor.

Bioreactor 10 further includes an apparatus for capturing the hydrogen containing gas produced by the hydrogen producing microorganisms. Capture and cleaning methods can vary widely within the spirit of the invention. In the present embodiment, as shown in FIG. 1, gas is removed from bioreactor 10 through passage 38, wherein passage 38 is any passage known in the art suitable for conveying a gaseous product. Pump 40 is operably related to passage 38 to aid the removal of gas from bioreactor 10 while maintaining a slight negative pressure in the bioreactor. In preferred embodiments, pump 40 is an air driven pump. The gas is conveyed to gas scrubber 42, where hydrogen is separated from carbon dioxide. Other apparatuses for separating hydrogen from carbon dioxide may likewise be used. The volume of collected gas can be measured by water displacement before and after scrubbing with concentrated NaOH. Samples of scrubbed and dried gas may be analyzed for hydrogen and methane by gas chromatography with a thermal conductivity detector (TCD) and/or with a flame ionization detector (FID). Both hydrogen and methane respond in the TCD, but the response to methane is improved in the FID (hydrogen is not detected by an FID, which uses hydrogen as a fuel for the flame).

Exhaust system 70 exhausts gas. Any exhaust system known in the art can be used. In a preferred embodiment, as shown in FIG. 1, exhaust system includes exhaust passage 72, backflow preventing device 74, gas flow measurement and totalizer 76, air blower 46 and exhaust pipe 78.

The organic feed material may be further inoculated in an initial inoculation step with one or a multiplicity of hydrogen producing microorganisms, such as *Clostridium sporogenes, Bacillus lichenformis* and *Kleibsiella oxytoca,* while contained in bioreactor 10. These hydrogen producing microorganisms are obtained from a bacterial culture lab or like source. Alternatively, the hydrogen producing microorganisms that occur naturally in the organic feed material can be used without inoculating the organic feed material.

In the present embodiment, the preferred hydrogen producing microorganisms is *Kleibsiella oxytoca*, a facultative enteric bacterium capable of hydrogen generation. *Kleibsiella oxytoca* produces a substantially 1:1 ratio of hydrogen to carbon dioxide through organic feed material metabolization, not including impurities. *Kleibsiella oxytoca* is typically already present in the organic feed material. Alternatively or additionally, the bioreactor may be directly inoculated with *Kleibsiella oxytoca*. In one embodiment, the inoculum for the bioreactor is a 48 h culture in nutrient broth added to diluted grape juice and the biorector was operated until gas production commenced. The bioreactor contents were not stripped of oxygen before or after inoculation.

In further embodiments, a carbon-based baiting material is provided within bioreactor 10 as shown FIG. 4. In this embodiment, the apparatus further includes a carbon-based baiting material 92, wherein the carbon based material is preferably coated on the one or a multiplicity of substrates 90 within bioreactor 10. The coating baits microorganisms contained in the organic feed material, which then grow thereon.

Carbon based baiting material 92 is preferably a gelatinous matrix having at least one carbon compound. In one embodiment, the gelatinous matrix is alginate or matrix based. In this embodiment, the gelatinous matrix is prepared by placing agar and a carbon compound into distilled water, wherein the agar is a gelatinous mix, and wherein any other gelatinous mix known in the art can be used in place of or in addition to agar within the spirit of the invention.

The carbon compound used with the gelatinous mix to form the gelatinous matrix can vary widely within the spirit of the invention. The carbon source is preferably selected from the group consisting of: glucose fructose, glycerol, mannitol, asparagines, casein, adonitol, l-arabinose, cellobiose, dextrose, dulcitol, d-galactose, inositol, lactose, levulose, maltose, d-mannose, melibiose, raffinose, rhamnose, sucrose, salicin, d-sorbitol, d-xylose or any combination thereof. Other carbon compounds known in the art, however, can be used within the spirit of the invention.

Generally, the matrix is formed by adding a ratio of three grams of carbon compound and two grams of agar per 100 mL of distilled water. This ratio can be used to form any amount of a mixture up to or down to any scale desired. Once the correct ratio of carbon compound, agar and water are mixed, the mixture is boiled and steam sterilized to form a molten gelatinous matrix. The gelatinous matrix is kept warm within a container such that the mixture remains molten. In one embodiment, the gelatinous matrix is held within a holding container in proximity to substrates 90 until needed to coat the substrates.

The one or a multiplicity of substrates can be any object, shape or material with a hollow or partially hollow interior, wherein the substrate further includes holes that connect the hollow or partially hollow interior to the surface of the substrate. The substrate must also have the ability to withstand heat tip to about 110° C. General representative objects and shapes include pipes, rods, beads, slats, tubes, slides, screens, honeycombs, spheres, objects with latticework, or other objects with holes or passages bored through the surface.

In one embodiment, the one or a multiplicity of substrates 90 are generally inserted into the bioreactor through corresponding slots, such that the substrates can be added or removed from the bioreactor without otherwise opening the bioreactor. In alternate embodiments, the substrates are affixed to an interior surface of the bioreactor.

In one embodiment, the one or a multiplicity of substrates are coated by carbon based coating material 92. The substrate can be coated by hand, by machine or by any means known in the art. In one embodiment, the carbon based coating material 92 may be coated directly onto the substrate. In alternative embodiments, however, an adhesive layer may be located between the carbon based coating material 92 and the substrate, the adhesive being any adhesive known in the art for holding carbon based compounds. In a preferred embodiment, the adhesive includes a plurality of gel beads, wherein carbon based coating material 92 is affixed to the gel beads ionically or by affinity.

In additional embodiments, coating material 92 is conveyed from the container holding carbon based coating material 92 into a hollow or partially hollow interior channel of the substrate. The gelatinous matrix is conveyed into the channel with a conveying device, preferably a pump. The conveying device can be any pumping means known in the art, including hand or machine. The carbon based coating material 92 permeates from the channel of the substrate to the exterior through the holes, coating the substrate surface. The carbon based coating material 92 on the substrate can be continually replenished at any time by conveying more gelatinous matrix into the interior of the substrate. The flow of carbon based coating material 92 can be regulated by the conveying device such that the substrate is coated and/or replenished at any speed or rate desired. Further, the entire substrate need not be covered by the carbon based coating material 92, although preferably the majority of the substrate is covered at any moment in time.

In further embodiments, the invention provides a system for producing hydrogen and isolating microorganisms having anaerobic bioreactor for holding organic feed material, one or a multiplicity of substrates contained within the bioreactor, the one or a multiplicity of substrates having a coating disposed thereon for hosting the growth of biofilm, wherein the coating is a replenishable coating from a coating source outside the bioreactor. The coating is contained in a coating container or other container proximate the bioreactor. The system further contains a passage connecting the coating container and the interior channel of one or a multiplicity of substrates. Coating is pumped from the coating container through the passage and into the channel, where the coating permeates from the channel through a permeable or semi-permeable surface of the substrates. As the coating permeates to the surface, it replenishes, i.e., supplements or replaces, coatings already present on the substrates. Alternatively, if no coating is present, the coating permeates to provide an initial coating on the substrates. By replenishing coating, the system has a continuous supply of bait and feeding material for microorganisms. The microorganisms for biofilm on the coated substrates and are thereby isolated on the substrates.

In further embodiments, the one or a multiplicity of substrates are replaceably insertable through openings in the bioreactor. The insertions maintain the anaerobic environment of the bioreactor.

The substrate provides an environment for the development and multiplication of microorganisms in the bioreactor, such as hydrogen producing microorganisms. This is advantageous as substrates enable microorganisms to obtain more nutrients and expend less energy than a similar microorganism floating loosely in organic feed material.

The microorganisms, baited by the carbon based coating material, attach themselves to the substrate, thereby forming a slime layer on the substrate generally referred to as a biofilm. The combination of carbon based coating material 92 on the substrate and the environmental conditions favorable to growth in the organic feed material allows the microorganisms to grow, multiply and form biofilms on the substrate.

In order to increase growth and concentration on the substrate coated with a carbon based baiting means for microorganisms, the surface area of the substrate can be increased. Increasing the surface area can be achieved by optimizing the surface area of a single substrate within the bioreactor, adding a multiplicity of substrates within the bioreactor, or a combination of both.

The apparatus may further include a coating of alginate within the interior of the bioreactor. The thickness and type of alginate coating can vary within the bioreactor. Thus, the bioreactor may have levels of alginate, i.e., areas of different formulations and amounts of alginate in different locations within the bioreactor.

Figure 5:
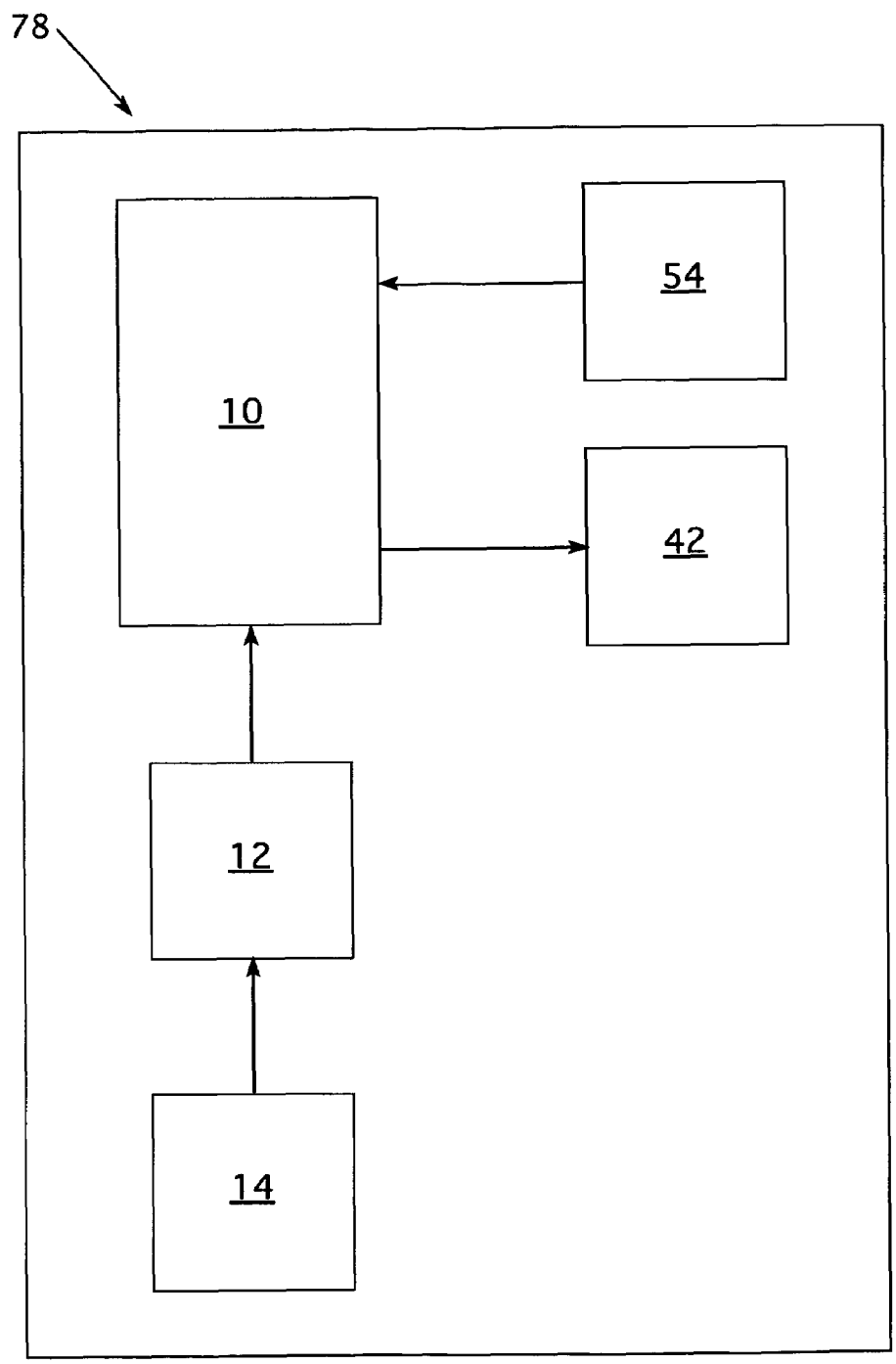
FIG. 5 is a top plan view of a system layout in a housing unit.

The system may be housed in a single housing unit 78 as shown in FIG. 5. The containers and bioreactors will be filled with liquid and thus will be heavy. For example, if a 300 gallon cone-bottom bioreactor is used, the bioreactor can weigh about 3,000 lbs. The stand preferably has four legs, with a 2" steel plate tying the legs together. If it is assumed that each leg rests on a 2×2 square, then the loading to the floor at those spots would be 190 lbs/sq inch. The inside vertical clearance is preferably at least 84 inches. For safety reasons, the main light switch for the building will be mounted on the outside next to the entry door and the electrical panel will be mounted on the exterior of the building so that all power to the building could be cut without entering. In this further preferred embodiment, the system is preferably proximate to industrial facility.

Hydrogen gas is flammable, but the ignition risk is low, and less than if dealing with gasoline or propane. Hydrogen gas is very light, and will rise and dissipate rapidly. A housing unit is preferably equipped with a vent ridge and eave vents creating natural ventilation. While the LEL (lower explosive limit) for hydrogen is 4%, it is difficult to ignite hydrogen even well above the LEL through electrical switches and motors.

All plumbing connections for the system are water tight, and the gas-side connections are pressure checked. Once the produced gas has been scrubbed of $CO_2$, it will pass through a flow sensor and then be exhausted to the atmosphere through a stand pipe. A blower (as used in boats where gas fumes might be present) will add air to the stand pipe at a rate of more than 500 to 1, thus reducing the hydrogen concentration well below the LEL. As soon as this mixture reaches the top of the pipe, it will be dissipated by the atmosphere.

In case of a leak inside the building, the housing unit preferably includes a hydrogen sensor connected to a relay which will activate an alarm and a ventilation system. The ventilation system is preferably mounted on the outside of the building and will force air through the building and out the roof vents. The hydrogen sensor is preferably set to activate if the hydrogen concentration reaches even 25% of the LEL. The only electrical devices will be a personal computer, low-voltage sensors, electrical outlets and connections, all of which will be mounted on the walls lower than normal. The hydrogen sources will preferably be located high in the room and since hydrogen does not settle.

EXAMPLE 1

A multiplicity of bioreactors were initially operated at pH 4.0 and a flow rate of 2.5 mL min$^{-1}$, resulting in a hydraulic retention time (HRT) of about 13 h (0.55 d). This is equivalent to a dilution rate of 1.8 d$^{-1}$. After one week all six bioreactors were at pH 4.0, the ORP ranged from −300 to −450 mV, total gas production averaged 1.6 L d$^{-1}$ and hydrogen production averaged 0.8 L d$^{-1}$. The mean COD of the organic feed material during this period was 4,000 mg L$^{-1}$ and the mean effluent COD was 2,800 mg L$^{-1}$, for a reduction of 30%. After one week, the pHs of certain bioreactors were increased by one half unit per day until the six bioreactors were established at different pH levels ranging from 4.0 to 6.5. Over the next three weeks at the new pH settings, samples were collected and analyzed each weekday. It was found that the optimum for gas production in this embodiment was pH 5.0 at 1.48 L hydrogen d$^{-1}$ (Table 2). This was equivalent to about 0.75 volumetric units of hydrogen per unit of bioreactor volume per day.

TABLE 2

Production of hydrogen in 2-L anaerobic bioreactors as a function of pH.

| pH | Total gas L/day | H2 L/day | H2 L/g COD | H2 per Sugar moles/mole |
|---|---|---|---|---|
| 4.0[a] | 1.61 | 0.82 | 0.23 | 1.81 |
| 4.5[b] | 2.58 | 1.34 | 0.23 | 1.81 |
| 5.0[c] | 2.74 | 1.48 | 0.26 | 2.05 |
| 5.5[d] | 1.66 | 0.92 | 0.24 | 1.89 |
| 6.0[d] | 2.23 | 1.43 | 0.19 | 1.50 |
| 6.5[e] | 0.52 | 0.31 | 0.04 | 0.32 |

[a]mean of 20 data points
[b]mean of 14 data points
[c]mean of 11 data points
[d]mean of 7 data points
[e]mean of 6 data points Also shown in Table 2 is the hydrogen production rate per g of COD, which also peaked at pH 5.0 at a value of 0.26 L g$^{-1}$ COD consumed. To determine the molar production rate, it was assumed that each liter of hydrogen gas contained 0.041 moles, based on the ideal gas law and a temperature of 25° C. Since most of the nutrient value in the grape juice was simple sugars, predominantly glucose and fructose (Table 1 above), it was assumed that the decrease in COD was due to the metabolism of glucose. Based on the theoretical oxygen demand of glucose (1 mole glucose to 6 moles oxygen), one gram of COD is equivalent to 0.9375 g of glucose. Therefore, using those conversions, the molar $H_2$ production rate as a function of pH ranged from 0.32 to 2.05 moles of $H_2$ per mole of glucose consumed. As described above, the pathway appropriate to these microorganisms results in two moles of $H_2$ per mole of glucose, which was achieved at pH 5.0. The complete data set is provided in Tables 3a and 3b.

Samples of biogas were analyzed several times per week from the beginning of the study, initially using a Perkin Elmer Autosystem GC with TCD, and then later with a Perkin Elmer Clarus 500 GC with TCD in series with an FID.

TABLE 3a

Bioreactor Operating Data

| Date | Reactor | collection hours | GAS Total volume (mL) | GAS after scrubbing (mL) | Liquid Readings Effluent (mL) | Liquid Readings NaOH (mL) | Liquid Readings Net Feed (mL) | ORP | pH | COD Feed (mg/L) | COD Effluent (mg/L) | COD Removal (mg/L) | Loading (g) | Consumed (g) | Performance Total gas L/day | Performance H2 L/day | Performance H2 L/g COD |
|---|---|---|---|---|---|---|---|---|---|---|---|---|---|---|---|---|---|
| 14-Nov | A | 5 | 540 | 220 | 780 | 0 | 780 | −408 | 4.0 | 4,480 | 2,293 | 2,187 | 3.494 | 1.706 | 2.59 | 1.06 | 0.13 |
| 14-Nov | B | 5 | 380 | 220 | 840 | 0 | 840 | −413 | 4.1 | 4,480 | 2,453 | 2,027 | 3.763 | 1.702 | 1.82 | 1.06 | 0.13 |
| 14-Nov | C | 5 | 350 | 170 | 870 | 0 | 870 | −318 | 4.1 | 4,480 | 2,293 | 2,187 | 3.898 | 1.902 | 1.68 | 0.82 | 0.09 |
| 14-Nov | D | 5 | 320 | 130 | 920 | 0 | 920 | −372 | 4.1 | 4,480 | 1,920 | 2,560 | 4.122 | 2.355 | 1.54 | 0.62 | 0.06 |
| 14-Nov | E | 5 | 240 | 100 | 920 | 0 | 920 | −324 | 4.3 | 4,480 | 2,773 | 1,707 | 4.122 | 1.570 | 1.15 | 0.48 | 0.06 |
| 14-Nov | F | 5 | 50 | 25 | 810 | 0 | 810 | −329 | 4.0 | 2,307 | 2,080 | 1,227 | 2.679 | 0.994 | 0.24 | 0.12 | 0.03 |
| 15-Nov | A | 5.5 | 450 | 230 | 1120 | 25 | 1095 | −400 | 4.0 | 3,307 | 3,787 | (480) | 3.621 | −0.525 | 1.96 | 1.00 | −0.44 |
| 15-Nov | B | 5.5 | 450 | 235 | 1180 | 35 | 1145 | −384 | 4.0 | 3,307 | 3,253 | 54 | 3.787 | 0.061 | 1.96 | 1.03 | 3.82 |
| 15-Nov | C | 5.5 | 250 | 130 | 640 | 0 | 640 | −278 | 4.0 | 3,307 | 3,520 | (213) | 2.116 | −0.136 | 1.09 | 0.57 | −0.95 |
| 15-Nov | E | 5.5 | 455 | 225 | 1160 | 0 | 1160 | −435 | 4.0 | 3,307 | 3,467 | (160) | 3.836 | −0.185 | 1.99 | 0.98 | −1.21 |
| 15-Nov | F | 5.5 | 430 | 235 | 1160 | 0 | 1160 | −312 | 4.0 | 3,307 | 3,413 | (106) | 3.836 | −0.123 | 1.88 | 1.03 | −1.91 |
| 16-Nov | A | 5 | 380 | 190 | 1020 | 27 | 993 | −414 | 4.0 | 4,693 | 3,627 | 1,066 | 4.660 | 1.059 | 1.82 | 0.91 | 0.18 |
| 5-Dec | A | 4.5 | 200 | 110 | 500 | 35 | 465 | −439 | 4.0 | 4,267 | 4,160 | 107 | 1.984 | 0.050 | 1.07 | 0.59 | 2.21 |
| 18-Nov | A | 5 | 360 | 190 | 200 | 0 | 200 | −423 | 4.0 | 3,680 | 5,227 | (1,547) | 0.736 | −0.309 | 1.73 | 0.91 | −0.61 |
| 21-Nov | A | 4 | 320 | 170 | 800 | 40 | 760 | −429 | 4.0 | 3,493 | 3,680 | (187) | 2.656 | −0.142 | 1.92 | 1.02 | −1.20 |
| 22-Nov | A | 3.75 | 285 | 190 | 725 | 21 | 704 | −432 | 4.0 | 4,107 | 2,293 | 1,813 | 2.891 | 1.277 | 1.82 | 1.22 | 0.15 |
| 29-Nov | A | 4.25 | 310 | 155 | 750 | 24 | 726 | −439 | 4.0 | 5,013 | 3,520 | 1,493 | 3.640 | 1.084 | 1.75 | 0.88 | 0.14 |
| 2-Dec | A | 3.75 | 250 | 120 | 660 | 26 | 634 | −438 | 4.0 | 4,587 | 3,893 | 694 | 2.908 | 0.440 | 1.60 | 0.77 | 0.27 |
| 6-Dec | A | 3 | 150 | 75 | 540 | 0 | 540 | −441 | 4.0 | 4,853 | 3,093 | 1,760 | 2.621 | 0.950 | 1.20 | 0.60 | 0.08 |
| 17-Nov | A | 5.5 | 330 | 160 | 1010 | 30 | 980 | −414 | 4.0 | 4,907 | 3,520 | 1,387 | 4.809 | 1.359 | 1.31 | 0.70 | 0.12 |
| averages | | 4.81 | 324 | 164 | 830 | 13 | 817 | −392 | 4.0 | 4,092 | 3,213 | 879 | 3.344 | 0.718 | 1.61 | 0.82 | 0.23 |
| 16-Nov | B | 5 | 400 | 200 | 1125 | 45 | 1080 | −397 | 4.5 | 4,693 | 3,520 | 1,173 | 5.068 | 1.267 | 1.92 | 0.96 | 0.16 |

TABLE 3a-continued

Bioreactor Operating Data

| | | | GAS | | Liquid Readings | | | | | COD | | | | Performance | | |
|---|---|---|---|---|---|---|---|---|---|---|---|---|---|---|---|---|
| Date | Reactor | collection hours | Total volume (mL) | after scrubbing (mL) | Effluent (mL) | NaOH (mL) | Net Feed (mL) | ORP | pH | Feed (mg/L) | Effluent (mg/L) | Removal (mg/L) | Loading (g) | Consumed (g) | Total gas L/day | H2 L/day | H2 L/g COD |
| 16-Nov | D | 5 | 400 | 165 | 960 | 60 | 900 | −360 | 4.5 | 4,693 | 3,573 | 1,120 | 4.224 | 1.008 | 1.92 | 0.79 | 0.16 |
| 16-Nov | E | 5 | 490 | 240 | 1100 | 72 | 1028 | −324 | 4.5 | 4,693 | 3,413 | 1,280 | 4.824 | 1.315 | 2.35 | 1.15 | 0.18 |
| 1-Dec | B | 3.5 | 500 | 260 | 570 | 45 | 525 | −415 | 4.5 | 5,173 | 3,680 | 1,493 | 2.716 | 0.784 | 3.43 | 1.78 | 0.33 |
| 6-Dec | B | 3 | 470 | 240 | 650 | 40 | 610 | −411 | 4.5 | 4,853 | 3,360 | 1,493 | 2.960 | 0.911 | 3.76 | 1.92 | 0.26 |
| 21-Nov | B | 4 | 560 | 300 | 930 | 50 | 880 | −397 | 4.5 | 3,493 | 3,147 | 346 | 3.074 | 0.305 | 3.36 | 1.80 | 0.98 |
| 2-Dec | B | 3.75 | 640 | 320 | 830 | 50 | 780 | −407 | 4.5 | 4,587 | 3,413 | 1,174 | 3.578 | 0.915 | 4.10 | 2.05 | 0.35 |
| 17-Nov | B | 5.5 | 450 | 220 | 1165 | 50 | 1115 | −406 | 4.5 | 4,907 | 2,933 | 1,974 | 5.471 | 2.201 | 1.96 | 0.96 | 0.10 |
| 18-Nov | B | 5 | 390 | 220 | 860 | 42 | 818 | −406 | 4.5 | 3,680 | 2,960 | 720 | 3.010 | 0.589 | 1.87 | 1.06 | 0.37 |
| 22-Nov | B | 3.75 | 585 | 395 | 835 | 50 | 785 | −397 | 4.5 | 4,107 | 2,720 | 1,387 | 3.224 | 1.089 | 3.74 | 2.53 | 0.36 |
| 29-Nov | B | 4.25 | 620 | 320 | 920 | 42 | 878 | −410 | 4.5 | 5,013 | 3,307 | 1,707 | 4.402 | 1.498 | 3.50 | 1.81 | 0.21 |
| 5-Dec | B | 4.5 | 390 | 190 | 750 | 37 | 713 | −417 | 4.5 | 4,267 | 3,840 | 427 | 3.042 | 0.304 | 2.08 | 1.01 | 0.62 |
| 16-Nov | F | 5 | 400 | 200 | 1082 | 93 | 989 | −324 | 4.5 | 4,693 | 3,093 | 1,600 | 4.641 | 1.582 | 1.92 | 0.96 | 0.13 |
| 16-Nov | C | 5 | 400 | 200 | 950 | 74 | 876 | −325 | 4.6 | 4,693 | 2,933 | 1,760 | 4.111 | 1.541 | 1.92 | 0.96 | 0.13 |
| averages | | 4.45 | 478 | 248 | 909 | 54 | 856 | −385 | 4.5 | 4,539 | 3,278 | 1,261 | 3.883 | 1.079 | 2.58 | 1.34 | 0.23 |

TABLE 3b

Bioreactor Operating Data Continued.

| | | | GAS | | Liquid Readings | | | | | COD | | | | Performance | | |
|---|---|---|---|---|---|---|---|---|---|---|---|---|---|---|---|---|
| Date | Reactor | collection hours | Tot volume (mL) | after scrubbing (mL) | Effluent (mL) | NaOH (mL) | Net Feed (mL) | ORP | pH | Feed (mg/L) | Effluent (mg/L) | Removal (mg/L) | Loading (g) | Consumed (g) | Total gas L/day | H2 L/day | H2 L/g COD |
| 17-Nov | C | 5.5 | 360 | 200 | 840 | 120 | 720 | −344 | 4.9 | 4,907 | 2,880 | 2,027 | 3.533 | 1.459 | 1.57 | 0.87 | 0.14 |
| 18-Nov | C | 5 | 370 | 200 | 1120 | 70 | 1050 | −328 | 4.9 | 3,680 | 2,480 | 1,200 | 3.864 | 1.260 | 1.78 | 0.96 | 0.16 |
| 29-Nov | C | 4.25 | 415 | 200 | 920 | 50 | 870 | −403 | 4.9 | 5,013 | 3,093 | 1,920 | 4.362 | 1.670 | 2.34 | 1.13 | 0.12 |
| 17-Nov | E | 5.5 | 490 | 270 | 1210 | 115 | 1095 | −352 | 5.0 | 4,907 | 4,747 | 160 | 5.373 | 0.175 | 2.14 | 1.18 | 1.54 |
| 1-Dec | D | 3.5 | 540 | 250 | 710 | 85 | 625 | −395 | 5.0 | 5,173 | 3,573 | 1,600 | 3.233 | 1.000 | 3.70 | 1.71 | 0.25 |
| 17-Nov | F | 5.5 | 475 | 225 | 1120 | 130 | 990 | −367 | 5.0 | 4,907 | 3,760 | 1,147 | 4.858 | 1.135 | 2.07 | 0.98 | 0.20 |
| 5-Dec | D | 4.5 | 580 | 310 | 710 | 77 | 633 | −423 | 5.0 | 4,267 | 3,573 | 694 | 2.701 | 0.439 | 3.09 | 1.65 | 0.71 |
| 6-Dec | D | 3 | 450 | 240 | 490 | 43 | 447 | −420 | 5.0 | 4,853 | 3,253 | 1,600 | 2.169 | 0.715 | 3.60 | 1.92 | 0.34 |
| 17-Nov | D | 3.5 | 680 | 415 | 580 | 83 | 497 | −326 | 5.0 | 4,907 | 4,213 | 694 | 2.439 | 0.345 | 4.66 | 2.85 | 1.20 |
| 2-Dec | D | 3.75 | 640 | 340 | 830 | 66 | 764 | −412 | 5.0 | 4,587 | 3,787 | 800 | 3.504 | 0.611 | 4.10 | 2.18 | 0.56 |
| 22-Nov | C | 3.75 | 460 | 295 | 800 | 50 | 750 | −349 | 5.0 | 4,107 | 1,280 | 2,827 | 3.080 | 2.120 | 2.94 | 1.89 | 0.14 |
| averages | | 4.34 | 496 | 268 | 848 | 81 | 767 | −374.5 | 5.0 | 4,664 | 3,331 | 1,333 | 3.579 | 1.023 | 2.74 | 1.48 | 0.26 |
| 5-Dec | C | 4.5 | 470 | 250 | 900 | 103 | 797 | −429 | 5.4 | 4,267 | 3,413 | 854 | 3.401 | 0.680 | 2.51 | 1.33 | 0.37 |
| 18-Nov | F | 5 | 90 | 45 | 600 | 55 | 545 | −451 | 5.5 | 3,680 | 3,440 | 240 | 2.006 | 0.131 | 0.43 | 0.22 | 0.34 |
| 21-Nov | D | 4 | 130 | 70 | 830 | 80 | 750 | −454 | 5.5 | 3,493 | 3,360 | 133 | 2.620 | 0.100 | 0.78 | 0.42 | 0.70 |
| 22-Nov | D | 3.75 | 360 | 250 | 766 | 69 | 696 | −461 | 5.5 | 4,107 | 2,880 | 1,227 | 2.858 | 0.854 | 2.30 | 1.60 | 0.29 |
| 29-Nov | D | 4.25 | 100 | 50 | 940 | 100 | 840 | −456 | 5.5 | 5,013 | 3,307 | 1,707 | 4.211 | 1.434 | 0.56 | 0.28 | 0.03 |
| 2-Dec | C | 3.75 | 560 | 290 | 810 | 93 | 717 | −430 | 5.5 | 4,587 | 3,573 | 1,014 | 3.289 | 0.727 | 3.52 | 1.86 | 0.40 |
| 6-Dec | C | 3 | 250 | 130 | 570 | 45 | 525 | −428 | 5.5 | 4,853 | 3,627 | 1,226 | 2.548 | 0.644 | 2.00 | 1.04 | 0.20 |
| averages | | 4.04 | 279 | 155 | 774 | 78 | 696 | −444.1 | 5.5 | 4,286 | 3,371 | 914 | 2.982 | 0.636 | 1.66 | 0.92 | 0.24 |
| 21-Nov | E | 4 | 360 | 250 | 930 | 130 | 800 | −400 | 6.0 | 3,493 | 2,987 | 506 | 2.794 | 0.405 | 2.10 | 1.50 | 0.62 |
| 22-Nov | E | 3.75 | 380 | 280 | 820 | 127 | 693 | −411 | 6.0 | 4,107 | 2,453 | 1,653 | 2.846 | 1.146 | 2.43 | 1.79 | 0.24 |
| 29-Nov | E | 4.25 | 360 | 230 | 870 | 71 | 799 | −467 | 6.0 | 5,013 | 1,973 | 3,040 | 4.006 | 2.429 | 2.03 | 1.30 | 0.09 |
| 1-Dec | E | 3.5 | 420 | 250 | 770 | 127 | 643 | −471 | 6.0 | 5,173 | 2,933 | 2,240 | 3.326 | 1.440 | 2.88 | 1.71 | 0.17 |
| 2-Dec | E | 3.75 | 280 | 170 | 540 | 85 | 455 | −443 | 6.0 | 4,587 | 3,360 | 1,227 | 2.087 | 0.558 | 1.79 | 1.09 | 0.30 |
| 5-Dec | E | 4.5 | 410 | 240 | 930 | 156 | 774 | −487 | 6.0 | 4,267 | 3,253 | 1,014 | 3.303 | 0.785 | 2.19 | 1.28 | 0.31 |
| 6-Dec | E | 3 | 380 | 170 | 660 | 105 | 555 | −490 | 6.0 | 4,853 | 2,293 | 2,560 | 2.693 | 1.421 | 2.24 | 1.36 | 0.12 |
| averages | | 3.82 | 354 | 227 | 789 | 114 | 674 | −453 | 6.0 | 4,499 | 2,750 | 1,749 | 3.033 | 1.179 | 2.23 | 1.43 | 0.19 |
| 29-Nov | F | 4.25 | 90 | 45 | 870 | 150 | 720 | −501 | 6.5 | 5,013 | 1,707 | 3,307 | 3.610 | 2.381 | 0.51 | 0.25 | 0.02 |
| 2-Dec | F | 3.75 | 20 | 0 | 810 | 136 | 674 | −497 | 6.5 | 4,587 | 3,573 | 1,014 | 3.092 | 0.683 | 0.13 | 0.00 | 0.00 |
| 22-Nov | F | 3.75 | 120 | 105 | 790 | 128 | 662 | −477 | 6.5 | 4,107 | 2,240 | 1,867 | 2.719 | 1.236 | 0.77 | 0.67 | 0.08 |
| 5-Dec | F | 4.5 | 10 | 0 | 670 | 121 | 549 | −532 | 6.5 | 4,267 | 2,827 | 1,440 | 2.343 | 0.791 | 0.05 | 0.00 | 0.00 |
| 6-Dec | F | 3 | 60 | 50 | 480 | 90 | 390 | −515 | 6.5 | 4,853 | 2,240 | 2,613 | 1.893 | 1.019 | 0.48 | 0.40 | 0.05 |
| 21-Nov | F | 4 | 200 | 100 | 910 | 150 | 760 | −472 | 6.5 | 3,493 | 2,613 | 880 | 2.655 | 0.669 | 1.20 | 0.60 | 0.15 |
| averages | | 3.88 | 83 | 50 | 755 | 129 | 626 | −499 | 6.5 | 4,387 | 2,533 | 1,853 | 2.745 | 1.160 | 0.52 | 0.31 | 0.04 |

Methane was never detected with the TCD, but trace amounts were detected with the FID (as much as about 0.05%).

Over a ten-day period, the organic feed material was mixed with sludge obtained from a methane-producing anaerobic digester at a nearby wastewater treatment plant at a rate of 30 mL of sludge per 20 L of diluted grape juice. There was no observed increase in the concentration of methane during this period. Therefore, it was concluded that the preheating of the feed to 65° C. as described previously was effective in deactivating the microorganisms contained in the sludge. Hydrogen gas production rate was not affected (data not shown).

Using this example, hydrogen gas is generated using a microbial culture over a sustained period of time. The optimal pH for this culture consuming simple sugars from a simulated fruit juice bottling wastewater was found to be 5.0. Under these conditions, using plastic packing material to retain microbial biomass, a hydraulic residence time of about 0.5 days resulted in the generation of about 0.75 volumetric units of hydrogen gas per unit volume of bioreactor per day.

Whereas particular embodiments of this invention have been described above for purposes of illustration, it will be evident to those skilled in the art that numerous variations of the details of the present invention may be made without departing from the invention as defined in the appended claims.

SELECTED CITATIONS AND BIBLIOGRAPHY

Brosseau, J. D. and J. E. Zajic. 1982a. Continuous Microbial Production of Hydrogen Gas. Int. J. Hydrogen Energy 7(8): 623-628.

Brosseau, J. D. and J. E. Zajic. 1982ba. Hydrogen-gas Production with *Citrobacter intermedius* and *Clostridium pasteurianum*. J. Chem. Tech. Biotechnol. 32:496-502.

Iyer, P., M. A. Bruns, H. Zhang, S. Van Ginkel, and B. E. Logan. 2004. Hydrogen gas production in a continuous flow bioreactor using heat-treated soil inocula. Appl. Microbiol. Biotechnol. 89(1):119-127.

Kalia, V. C., et al. 1994. Fermentation of biowaste to H2 by *Bacillus licheniformis*. World Journal of Microbiol & Biotechnol. 10:224-227.

Kosaric, N. and R. P. Lyng. 1988. Chapter 5: Microbial Production of Hydrogen. In Biotechnology, Vol. 6B. editors Rehm & Reed. pp 101-137. Weinheim: Vett.

Logan, B. E., S.-E. Oh, I. S. Kim, and S. Van Ginkel. 2002. Biological hydrogen production measured in batch anaerobic respirometers. Environ. Sci. Technol. 36(11):2530-2535.

Logan, B. E. 2004. Biologically extracting energy from wastewater: biohydrogen production and microbial fuel cells. Environ. Sci. Technol., 38(9):160A-167A Madigan, M. T., J. M. Martinko, and J. Parker. 1997. *Brock Biology of Microorganisms, Eighth Edition,* Prentice Hall, N.J.

Nandi, R. and S. Sengupta. 1998. Microbial Production of Hydrogen: An Overview. Critical Reviews in Microbiology, 24(1):61-84.

Noike et al. 2002. Inhibition of hydrogen fermentation of organic wastes by lactic acid bacteria. International Journal of Hydrogen Energy. 27:1367-1372

Oh, S.-E., S. Van Ginkel, and B. E. Logan. 2003. The relative effectiveness of pH control and heat treatment for enhancing biohydrogen gas production. Environ. Sci. Technol. 37(22):5186-5190.

Prabha et al. 2003. $H_2$-Producing bacterial communities from a heat-treated soil Inoculum. Appl. Microbiol. Biotechnol. 66:166-173

Wang et al. 2003. Hydrogen Production from Wastewater Sludge Using a *Clostridium* Strain. J. Env. Sci. Health. Vol. A38(9):1867-1875

Yokoi et al. 2002. Microbial production of hydrogen from starch-manufacturing wastes. Biomass & Bioenergy; Vol. 22 (5):389-396.

What is claimed is:

1. A system for producing hydrogen and isolating microorganisms, comprising:
    an anaerobic bioreactor for holding organic feed material and adapted to produce hydrogen from hydrogen producing microorganisms metabolizing the organic feed material, and
    one or a multiplicity of substrates contained within the bioreactor, the one or a multiplicity of substrates having a coating disposed thereon, wherein the coating is a replenishable coating from a coating source outside the bioreactor.

2. The system of claim 1, wherein the coating is a gelatinous matrix coating.

3. The system of claim 2, wherein the gelatinous matrix is formed from agar and at least one carbon compound.

4. The system of claim 3, wherein the carbon compound is selected from the group consisting of glucose, fructose, glycerol, mannitol, asparagines, casein, adonitol, l-arabinose, cellobiose, dextrose, dulcitol, d-galactose, inositol, lactose, levulose, maltose, d-mannose, melibiose, raffinose, rhamnose, sucrose, salicin, d-sorbitol, d-xylose or combinations thereof.

5. The system of claim 1, wherein the one or a multiplicity of substrates are insertable through openings in the casing of the bioreactor, the substrates disposed through the openings to maintain the anaerobic environment.

6. The system of claim 1, wherein the one or a multiplicity of substrates have a permeable or semi-permeable surface portion and a channel portion interior the surface portion.

7. The system of claim 6, wherein additional coating is introduced into the channel portion of the one or a multiplicity of substrates, the additional coating permeating though the surface portion of the one or a multiplicity of substrates to replenish the replenishable coating.

8. The system of claim 6, wherein the one or a multiplicity of substrates are affixed to the bioreactor, the channel portion accessible from outside the bioreactor through one or a multiplicity of openings in the bioreactor.

9. The system of claim 1, wherein hydrogen producing microorganisms combine with the gelatinous matrix to form biofilm on the substrates.

10. The system of claim 1, wherein microorganisms combine with the gelatinous matrix to form biofilm on the substrates, thereby isolating the microorganisms.

11. The system of claim 1, wherein the organic feed material is heated to substantially kill or deactivate methanogens therein.

12. The system of claim 1, wherein the pH of the organic feed material in the bioreactor is controlled to a range of about 3.5-6.0 pH.

13. A system for producing hydrogen and isolating microorganisms, comprising:
    an anaerobic bioreactor for holding organic feed material and adapted to produce hydrogen from hydrogen producing microorganisms metabolizing the organic feed material.

one or a multiplicity of substrates contained within the bioreactor, the one or a multiplicity of substrates having a permeable or semi-permeable surface portion, a channel portion interior the surface portion, wherein the channel accessible from outside the bioreactor, a coating container for containing a coating, and a coating passage for conveying the coating from the coating container to the channel portions of the one or a multiplicity of substrates.

14. The system of claim 13, wherein the coating is a gelatinous matrix coating.

15. The system of claim 14, wherein the gelatinous matrix is formed from agar and a carbon compound.

16. The system of claim 15, wherein the carbon compound is selected from the list consisting of glucose, fructose, glycerol, mannitol, asparagines, casein, adonitol, l-arabinose, cellobiose, dextrose, dulcitol, d-galactose, inositol, lactose, levulose, maltose, d-mannose, melibiose, raffinose, rhamnose, sucrose, salicin, d-sorbitol, d-xylose or combinations thereof.

17. The system of claim 13, wherein the substrates are affixed to the bioreactor.

18. The system of claim 13, wherein the substrates are insertable through openings in the casing of the bioreactor, the substrates disposed through the openings to maintain the anaerobic environment.

19. The system of claim 13, wherein a coating pump is operably related to the coating passage.

20. The system of claim 13, wherein microorganisms combine with the gelatinous matrix to form biofilm on the substrates, thereby isolating the microorganisms.

* * * * *

UNITED STATES PATENT AND TRADEMARK OFFICE
CERTIFICATE OF CORRECTION

PATENT NO.       : 7,473,552 B2
APPLICATION NO.  : 11/449895
DATED            : January 6, 2009
INVENTOR(S)      : Justin Felder et al.

It is certified that error appears in the above-identified patent and that said Letters Patent is hereby corrected as shown below:

Column 1, line 58, first instance, "biodegredation" should be --biodegradation--.
Column 1, line 58, second instance, line 62 and lines 64-65, "Biodegredation" should be --Biodegradation--.
Column 1, line 59, "degredation" should be --degradation--.
Column 1, line 60, "material organic material" should be --organic material--.
Column 1, line 61, "bioremeduiation" should be --bioremediation--.
Column 1, line 63, "generallys" should be --generally--.
Column 1, line 66, "uneeded" should be --unneeded--.
Column 1, line 66, "natureal" should be --natural--.
Column 2, line 1, "hgreenhouse" should be --greenhouse--.
Column 3, line 11, "in an a system" should be --in a system--.
Column 3, lines 35-36, "a system a system" should be --a system--.
Column 3, line 49, "pump is operably" should be --pump which is operably--.
Column 3, line 51, "that a gelatinous" should be --that is a gelatinous--.
Column 3, line 55, "selected form" should be --selected from--.
Column 4, line 9, "plain view the bioreactor" should be --plain view of the bioreactor--.
Column 5, line 54, "a organic" should be --an organic--.
Column 8, line 63, "the sustain production" should be --the sustained production--.
Column 9, line 8, "operably" should be --operable--.
Column 9, line 22, "to grown biofilms." should be --to grow biofilms.--.
Column 9, line 32, "entry access provided is provided by" should be --entry access provided by--.
Column 9, line 42, "located of the bioreactor" should be --location of the bioreactor--.
Column 9, line 49, "but are to limited to," should be --but are not limited to--.
Column 9, line 58, "is all apparatus" should be --is an apparatus--.
Column 9, line 59, "a how of gas" should be --a flow of gas--.
Column 9, line 60, "Additionally chemical" should be --Additionally, chemical--.
Column 10, line 11, "additionally lo" should be --additionally to--.
Column 12, line 4, "lichenformis" should be --licheniformis--.
Column 12, line 20, "biorector" should be --bioreactor--.
Column 13, line 58, "for" should be --form--.
Column 14, line 67, "and since hydrogen" should be --since hydrogen--.

CERTIFICATE OF CORRECTION (continued)
U.S. Pat. No. 7,473,552 B2

The headings for Table 3a should be as follows:

Table 3a. Bioreactor Operating Data

| | | | GAS | | Liquid | | Readings | | COD | | | | | Performance | | |
|---|---|---|---|---|---|---|---|---|---|---|---|---|---|---|---|---|
| Date | Reactor | collection hours | Total volume (mL) | after scrubbing (mL) | Effluent (mL) | NaOH (mL) | Net Feed (mL) | ORP | pH | Feed (mg/L) | Effluent (mg/L) | Removal (mg/L) | Loading (g) | Consumed (g) | Total gas L/day | H2 L/day | H2 L/g COD |

In Table 3a, in the fourteenth column entitled "Loading (g)", line 15, "2.656" should be --2.655--.
In Table 3a, in the fourth column entitled "Total volume (mL)", line 20, "330" should be --300--.
In Table 3a, a solid line should begin in the space between "17-Nov" and "averages" (lines 20 and 21) and extend across the table.
In Table 3a (second page), a solid line should begin in the space between "16-Nov" (line 13) and "averages" (line 14) and extend across the table.

The headings for Table 3b should be as follows:

Table 3b. Bioreactor Operating Data Continued.

| | | | GAS | | Liquid | | Readings | | COD | | | | | Performance | | |
|---|---|---|---|---|---|---|---|---|---|---|---|---|---|---|---|---|
| Date | Reactor | collection hours | Tot volume (mL) | after scrubbing (mL) | Effluent (mL) | NaOH (mL) | Net Feed (mL) | ORP | pH | Feed (mg/L) | Effluent (mg/L) | Removal (mg/L) | Loading (g) | Consumed (g) | Total gas L/day | H2 L/day | H2 L/g COD |

In Table 3b, in the sixth column entitled "Effluent (mL)", line 16, "766" should be --765--.
In Table 3b, in the fourth column entitled "(collection hours)", line 27, "380" should be --280--.
In Table 3b, a solid line should begin in the space between "21-Nov" (line 34) and "averages" (line 35) and extend across the table.

Signed and Sealed this

Ninth Day of March, 2010

David J. Kappos
*Director of the United States Patent and Trademark Office*